(12) United States Patent
Gong et al.

(10) Patent No.: US 12,066,366 B2
(45) Date of Patent: Aug. 20, 2024

(54) TIME-VARYING DETECTING DEVICE AND METHOD FOR CONCRETE RHEOLOGICAL PARAMETERS

(71) Applicant: SHANGHAI CONSTRUCTION GROUP CO., LTD., Shanghai (CN)

(72) Inventors: Jian Gong, Shanghai (CN); Jun Xu, Shanghai (CN); Yonghe Xu, Shanghai (CN); Shengyi Wang, Shanghai (CN); Xiaowan Shi, Shanghai (CN)

(73) Assignee: SHANGHAI CONSTRUCTION GROUP CO., LTD., Shanghai (CN)

( * ) Notice: Subject to any disclaimer, the term of this patent is extended or adjusted under 35 U.S.C. 154(b) by 478 days.

(21) Appl. No.: 17/420,942

(22) PCT Filed: Jun. 25, 2019

(86) PCT No.: PCT/CN2019/092621
§ 371 (c)(1),
(2) Date: Jul. 6, 2021

(87) PCT Pub. No.: WO2020/140404
PCT Pub. Date: Jul. 9, 2020

(65) Prior Publication Data
US 2022/0091005 A1    Mar. 24, 2022

(30) Foreign Application Priority Data

Jan. 3, 2019  (CN) .......................... 201910004032.1

(51) Int. Cl.
*G01N 11/02* (2006.01)
*B01F 33/35* (2022.01)
(Continued)

(52) U.S. Cl.
CPC .............. *G01N 11/02* (2013.01); *B01F 33/35* (2022.01); *B01F 33/5011* (2022.01); *G01N 1/38* (2013.01);
(Continued)

(58) Field of Classification Search
CPC .... G01N 1/38; G01N 11/02; G01N 2001/386; G01N 2011/0033; G01N 2011/0046;
(Continued)

(56) References Cited

U.S. PATENT DOCUMENTS 4,095,288 A * 6/1978 Garlinghouse ......... B01F 31/31
366/343
9,914,101 B1 * 3/2018 Schrudder ......... B01F 33/50115
(Continued)

FOREIGN PATENT DOCUMENTS

CN            2068421 U    1/1991
CN          101403675 A    4/2009
(Continued)

OTHER PUBLICATIONS

English translation of CN10268298 accessed from worldwide.espacenet.com Nov. 4, 2021.*
(Continued)

*Primary Examiner* — Kristina M Deherrera
*Assistant Examiner* — Jean F Morello
(74) *Attorney, Agent, or Firm* — MUNCY, GEISSLER, OLDS & LOWE, P.C.

(57) ABSTRACT

A time-varying detecting device and method for concrete rheological parameters, in which the double-covered cylinder has top and bottom covers (11, 12), both of which can be freely opened, is configured to contain a concrete sample, and a lifting frame includes a pair of vertical supports (21) extending in parallel with each other. The double-covered cylindrical container is held between the pair of vertical (Continued)

supports (21) by means of connecting members (30) in such a manner that it can be flipped 180° about a straight line along which the connecting members (30) extend under the action of an external force. To perform a test, the top cover (11) is opened and a concrete mix is filled in, followed by detecting initial rheological parameters. The top cover (11) is closed, and the concrete mix is left for a predetermined period of time. The double-covered cylindrical container is lifted to a predetermined height by raising the connecting members (30), flipped 180° and lowered back onto the floor. The bottom cover (12) is opened, and the concrete mix is re-mixed and homogenized, followed by finally detecting the time-varying rheological parameters of the concrete mix.

5 Claims, 2 Drawing Sheets

(51) Int. Cl.
    *B01F 33/501* (2022.01)
    *B01F 101/28* (2022.01)
    *G01N 1/38* (2006.01)
    *G01N 11/00* (2006.01)
    *G01N 33/38* (2006.01)

(52) U.S. Cl.
    CPC ........ *G01N 33/383* (2013.01); *B01F 2101/28* (2022.01); *B01F 2215/0422* (2013.01); *G01N 2001/386* (2013.01); *G01N 2011/0033* (2013.01)

(58) Field of Classification Search
    CPC ............... G01N 33/383; B01F 2101/28; B01F 2215/0422; B01F 33/35; B01F 33/5011
    See application file for complete search history.

(56) References Cited

U.S. PATENT DOCUMENTS

| | | |
|---|---|---|
| 2005/0132782 A1 | 6/2005 | Wallevik |
| 2013/0062300 A1* | 3/2013 | Drake ................... A47F 5/0884 |
| | | 211/183 |
| 2014/0054251 A1* | 2/2014 | Lin ........................ G01N 3/303 |
| | | 211/183 |
| 2014/0311225 A1 | 10/2014 | Morgan |

FOREIGN PATENT DOCUMENTS

| | | | | |
|---|---|---|---|---|
| CN | 102608298 A | * | 7/2012 | |
| CN | 202506341 U | | 10/2012 | |
| CN | 103502793 A | | 1/2014 | |
| CN | 204405662 U | | 6/2015 | |
| CN | 106018178 A | | 10/2016 | |
| CN | 205627791 U | | 10/2016 | |
| CN | 106290104 A | | 1/2017 | |
| CN | 206493439 U | | 9/2017 | |
| CN | 206638554 U | | 11/2017 | |
| CN | 207415689 U | | 5/2018 | |
| CN | 108225939 A | * | 6/2018 | ............. G01N 3/062 |
| CN | 208068579 U | | 11/2018 | |
| CN | 108956381 A | | 12/2018 | |
| CN | 109387457 A | | 2/2019 | |
| EP | 3182093 A1 | | 6/2017 | |

OTHER PUBLICATIONS

English translation of CN108225939 accessed from worldwide. espacenet.com Nov. 4, 2021.*
Screenshot of L.K.Goodwin "Vertical-Lift Drum Pourers" dated Sep. 17, 2016, accessed using Waybackmachine https://web.archive.org/.*
Gao; "Influence of mineral admixtures on the rheological properties of self-compacting concrete"; Mar. 31, 2016; No. 2 vol. 46 Journal of Jilin University (Engineering and Technology Edition) ; (pp. 6).
Xiao; "Study on the Rheological Behavior of Cement-Limestone Powder Paste with Time"; Jan. 31, 2017; No. 1 vol. 36 Bulletin of the Chinese Ceramic Society; (pp. 7).

* cited by examiner

TIME-VARYING DETECTING DEVICE AND METHOD FOR CONCRETE RHEOLOGICAL PARAMETERS

TECHNICAL FIELD

The present invention relates to the technical field of concrete technology and, more specifically, to time-varying detecting device and method for concrete rheological parameters.

BACKGROUND

Contemporary research on rheological properties of concrete relies primarily on ICAR rheometers and is focusing on static/dynamic yield stress, dynamic plastic viscosity and time-varying behavior. Current methods for testing time-varying rheological parameters essentially involve keeping, in a testing container for a period of time (e.g., one or two hours), a fresh concrete mix that has undergone an initial measurement on rheological parameters and, upon expiry of this period (when the mix would have stratified and tends to have experienced water loss from evaporation), transferring the mix into a laboratory concrete mixer for re-mixing and homogenization. The remixed concrete is then poured into the testing container again, and the rheometer is activated to perform the same measurement to determine values indicating its time-varying rheological parameters. Although such devices and methods could be used to measure both initial rheological parameters and time-varying rheological parameters of concrete, they are time-consuming, labor-intensive, hard to ensure an accurate mixing ratio of concrete, complicated to operate and associated with significant potential safety hazards, especially in a remixing process carried out after concrete has been kept standing for a period of time.

Therefore, it is necessary to develop a time-varying detecting device and method for concrete rheological parameters, which can measure both the initial rheological parameters and the time-varying rheological parameters of a concrete mix in a simple, efficient, safe way and thus technically guarantee the smooth progress of the subsequent concrete pumping for construction.

The information disclosed in this Background section is only for enhancement of understanding of the general background of the invention and should not be taken as an acknowledgment or any form of suggestion that this information forms the prior art already known to a person skilled in the art.

SUMMARY OF THE INVENTION

It is an objective of the present invention to provide a time-varying detecting device and method for concrete rheological parameters, and especially, to create a novel time-varying detecting method for concrete rheological parameters and to develop a novel time-varying detecting device for concrete rheological parameters, which can measure and investigate rheological parameters of concrete in a simple, efficient, safe way and provide technical support for research on concrete rheology.

To achieve the above objective, the present invention provides a time-varying detecting device for concrete rheological parameters, which comprises:

a double-covered cylindrical container comprising a top cover and a bottom cover, each of which can be opened and closed freely, and a hollow cylindrical body;

a lifting frame comprising a pair of vertical supports arranged in such a way that a rotatable connection is established between each of the vertical supports and the respective side wall of the double-covered cylindrical container by a connecting member, such that the double-covered cylindrical container can be flipped 180° about a straight line along which the connecting members extend under the action of an external force. The connecting members are lifting rods, and recesses are symmetrically formed in an outer surface of the cylindrical body and provided with associated fasteners. Left bracket-shaped or ear-shaped slots are formed in central portions of the vertical supports. One end of each lifting rod is received in a respective one of the recesses and tightly locked by the fastener, and the other end is inserted in a respective one of the slots so that the lifting rod is slidable therein.

Compared with the prior art, the present invention provides the following technical benefits:

1. In the time-varying detecting device for concrete rheological parameters according to the present invention, the double-covered cylindrical container with the top and bottom covers that can be freely opened is configured to contain a concrete sample, and the two vertical supports of the lifting frame extend in parallel with each other. The double-covered cylindrical container that is held between the pair of vertical supports by the connecting members can be flipped 180° about a straight line along which the connecting members 30 extend under the action of an external force. To perform a test, the top cover is opened to form an opening and a concrete mix enters into the double-covered cylindrical container through the opening, followed by detecting the initial rheological parameters of the concrete mix. Then, the top cover is closed and the concrete mix is left for a period of time, and then the double-covered cylindrical container is pulled upward to flip 180° and lowered onto the floor. The bottom cover is now at the top. The bottom cover 12 is opened, and a handheld portable light-duty vane-type mixer is used to re-mix and homogenize the concrete in the double-covered cylindrical container. Finally, the time-varying rheological parameters of the concrete mix are detected. Therefore, the proposed device and method are much more efficient in detecting time-varying rheological parameters and simpler when compared with conventional methods and procedures. Moreover, it can greatly reduce the labor required for re-mixing and effectively ensure the personal safety of the involved engineers and technicians.

2. In the time-varying detecting device for concrete rheological parameters according to the present invention, the covers of the cylindrical container can effectively prevent water loss over time, ensuring an accurately maintained mixing ratio of concrete.

3. The time-varying detecting device for concrete rheological parameters according to the present invention is easy to operate, assemble and disassemble and can meet the field testing and verification requirements for construction sites.

Additionally, the device may further comprise diagonal braces, which are arranged in pairs at the bottom of the respective vertical supports.

Additionally, skirt bands may be vertically spaced from one another across an inner wall of the double-covered cylindrical container.

Additionally, the device may further comprise an associated portable light-duty vane-type mixer configured for quick re-mixing of a concrete mix that has been kept in the double-covered cylindrical container for a period of time.

The present invention further provides a time-varying detecting method for concrete rheological parameters according to the present invention, comprising the steps of:

Step 1: Providing a double-covered cylindrical container which has top and bottom covers, both of which can be freely opened and closed, and a lifting frame with a pair of vertical supports arranged in such a way that a rotatable connection is established between each of the vertical supports and the respective side wall of the double-covered cylindrical container by a connecting member. Ear-shaped slots are formed in central portions of the vertical supports. One end of each connecting member is received in a respective recess formed in an outer surface of the double-covered cylindrical container and tightly locked with an associated fastener, and the other end is inserted in a respective one of the slots.

Step 2: Opening the top cover of the double-covered cylindrical container to form an opening and filling a prepared concrete mix into the double-covered cylindrical container through the opening.

Step 3: Setting operating parameters of a rheometer and activate the rheometer to detect immediate data of static and dynamic rheological parameters of the fresh concrete mix, followed by deactivation of the rheometer.

Step 4: Tightly closing the top cover of the double-covered cylindrical container and leaving the double-covered cylindrical container until a predetermined period of time expires.

Step 5: Inserting and fixing opposing end portions of the lifting rods respectively in the vertical supports and the recesses in the outer surface of the double-covered cylindrical container, lifting the double-covered cylindrical container to a predetermined height by raising the lifting rods, flipping the double-covered cylindrical container 180°, and lowering the double-covered cylindrical container back onto the floor.

Step 6: Opening the bottom cover and re-mixing the concrete in the double-covered cylindrical container using a portable light-duty vane-type mixer until it becomes homogeneous.

Step 7: Repeating Step 3 to detect the time-varying rheological parameters of the concrete mix.

Step 8: Deactivating the rheometer and ending the test.

Additionally, the rheological parameters include plastic viscosity and yield stress.

Additionally, the predetermined period of time is preferred to be one hour, two hours or three hours.

Additionally, skirt bands are preferably vertically spaced from one another across an inner wall of the double-covered cylindrical container.

Additionally, in addition to the vertical plates, each of the vertical supports includes vertical plates and a foot plate to which the two vertical plates extending in parallel are connected at the bottom. Diagonal braces are provided where the vertical plates are connected to the foot plate.

In these figures, 11 denotes a top cover; 12, a bottom cover; 14, a skirt band; 21, a vertical support; 22, a diagonal brace; 23, a foot plate; and 30, a connecting member.

DETAILED DESCRIPTION

Time-varying detecting device and method for concrete rheological parameters provided in this invention will be described in greater detail below by way of specific examples with reference to the accompanying drawings. Features and advantages of the present invention will be more apparent from the following description, and from the appended claims. Note that the figures are provided in a very simplified form not necessarily drawn to exact scale for the only purpose of helping to explain the disclosed examples in a more convenient and clearer way. For the convenience of description, the terms "top" and "bottom" are used hereinafter in consistence with the orientation as shown in the figures, but this is not to be understood as a limitation of the scope of the present invention.

Embodiment 1

The structure and composition of a time-varying detecting device for concrete rheological parameters according to the present invention will be detailed below with combined reference to FIGS. 1 and 2.

Figure 1:
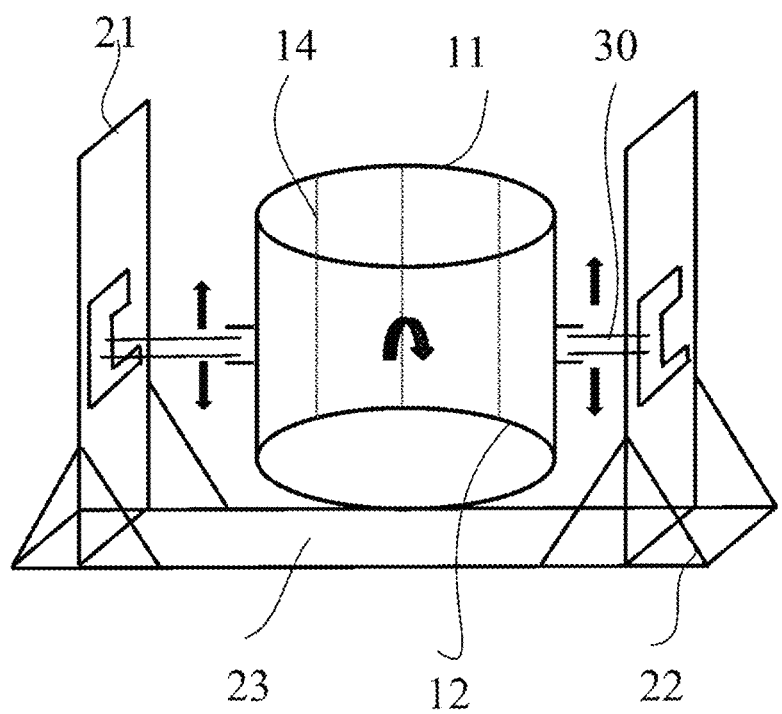
FIG. 1 schematically illustrates a time-varying detecting device for concrete rheological parameters according to Embodiment 1 of the present invention.
Figure 2:
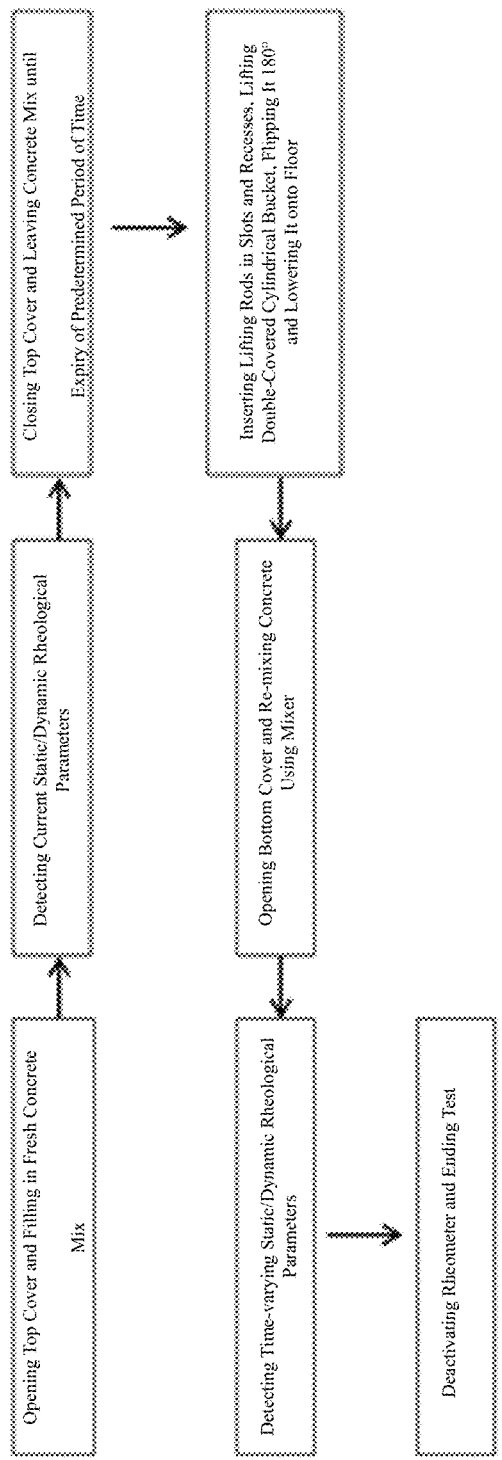
FIG. 2 is a flowchart of a time-varying detecting method for concrete rheological parameters according to Embodiment 1 of the present invention.

Referring to FIG. 1, the device includes a double-covered cylindrical container and a lifting frame. The double-covered cylindrical container includes a top cover 11 and a bottom cover 12, each of which can be opened and closed freely, and a hollow cylindrical body. The lifting frame includes a pair of vertical supports 21, each of which is rotatably connected by a connecting member 30 to a side wall of the double-covered cylindrical container. As such, under the action of an external force, the double-covered cylindrical container can be flipped 180° about a straight line along which the connecting members 30 extend. The connecting members 30 are lifting rods. Recesses are symmetrically formed in an outer surface of the cylindrical body at said locations and are provided with associated fasteners. Left bracket-shaped or ear-shaped slots are formed in central portions of the vertical supports 21. One end of each lifting rod is received in a respective one of the recesses and tightly locked by the fastener, and the other end is inserted in a respective one of the slots so that the lifting rod is slidable therein. The lifting rods may be implemented as round rods having a diameter same as that of the recesses.

Specifically, in the time-varying detecting device for concrete rheological parameters according to the present invention, the double-covered cylindrical container with the top and bottom covers 11, 12 that can be freely opened is configured to contain a concrete sample, and the two vertical supports 21 of the lifting frame extend in parallel with each other. The double-covered cylindrical container that is held between the pair of vertical supports 21 by the connecting members 30 can be flipped 180° about a straight line along which the connecting members 30 extend under the action of an external force. To perform a test, the top cover 11a is opened to form an opening, and a concrete mix enters into the double-covered cylindrical container through the opening, followed by detecting the initial rheological parameters of the concrete mix. Then, the top cover is closed, and the double-covered cylindrical container is flipped 180° and lowered onto the floor. The bottom cover is now at the top. The bottom cover 12 is opened, and a handheld portable light-duty vane-type mixer is used to re-mix and homogenize the concrete in the double-covered cylindrical container. Finally, the time-varying rheological parameters of the concrete mix are detected. A concrete mix may stratify over time into an upper mortar layer and a lower aggregate layer. At this point, it would be impossible to re-homogenize the concrete using a light-duty vane-type mixer unless it is flipped over to allow the aggregates to move downward by their own gravity and mix with the mortar. As a result, re-mixing and homogenization of the concrete mix that has been kept for a period of time become possible for a light-duty vane-type mixer. Therefore, the proposed device and method are much more efficient in detecting time-varying rheological parameters and simpler when compared with conventional methods and procedures. Moreover, it can greatly reduce the labor required for re-mixing and effectively ensure the personal safety of the involved engineers and technicians. The cylinder covers can effectively prevent water loss over time, thus ensuring an accurately maintained mixing ratio of concrete.

According to this embodiment, the device preferably includes diagonal braces 22, which are arranged in pairs at the bottom of the respective vertical supports 21.

According to this embodiment, in order to prevent slippage of concrete within the double-covered cylindrical container, skirt bands 14 are preferably vertically spaced from one another across an inner wall of the double-covered cylindrical container.

According to this embodiment, an associated portable light-duty vane-type mixer is preferably provided for quick re-mixing of a concrete mix that has been kept in the double-covered cylindrical container for a period of time. Of course, in order to facilitate homogenization, the concrete mix may be vibrated in advance using a vibrator if necessary.

In this embodiment, there is also provided a time-varying detecting method for concrete rheological parameters, which includes the steps as follows.

Step 1: Providing a double-covered cylindrical container which has top and bottom covers, both of which can be freely opened and closed, and a lifting frame with vertical supports 21 including a pair of vertical plates arranged in such a way that a rotatable connection is established between each of the vertical plates and the respective side wall of the double-covered cylindrical container by a connecting member 30. The connecting members 30 are lifting rods, and ear-shaped slots are formed in central portions of the vertical plates. One end of each lifting rod is received in a respective recess formed in an outer surface of the double-covered cylindrical container and tightly locked with an associated fastener, and the other end is inserted in a respective one of the slots.

Step 2: Opening the top cover 11 of the double-covered cylindrical container to form an opening and filling a prepared concrete mix into the double-covered cylindrical container through the opening. That is, a fresh concrete mix is filled in.

Step 3: Setting operating parameters of a rheometer and activate the rheometer to detect immediate data of static and dynamic rheological parameters of the fresh concrete mix, followed by deactivation of the rheometer.

Step 4: Tightly closing the top cover of the double-covered cylindrical container and leaving the double-covered cylindrical container until a predetermined period of time expires.

Step 5: Inserting and fixing opposing end portions of the lifting rods respectively in the vertical plates of the lifting frame and the recesses in the outer surface of the double-covered cylindrical container, lifting the double-covered cylindrical container to a predetermined height by raising the lifting rods, flipping the double-covered cylindrical container 180°, and lowering the double-covered cylindrical container back onto the floor.

Step 6: Opening the bottom cover 12 and re-mixing the concrete in the double-covered cylindrical container using a portable light-duty vane-type mixer until it becomes homogeneous.

Step 7: Repeating Step 3 to detect the time-varying rheological parameters of the concrete mix.

Step 8: Deactivating the rheometer and ending the test.

According to this embodiment, the rheological parameters preferably include plastic viscosity and yield stress.

According to this embodiment, the predetermined period of time is preferred to be one hour, two hours or three hours.

According to this embodiment, skirt bands 14 are preferably vertically spaced from one another across an inner wall of the double-covered cylindrical container.

According to this embodiment, in addition to the vertical plates, the vertical supports 21 preferably further include a foot plate 23 to which the two vertical plates extending in parallel are connected at the bottom. Diagonal braces 22 may be provided where the vertical plates are connected to the foot plate 23. In order for the vertical plates to be firmly connected to the foot plate 23, the connection may be accomplished by, without limitation, welding or threading. For considerations of material accessibility, cost and stress tolerance, the vertical plates are desirably rectangular and made of steel, aluminium alloy or another suitable material. Ear-shaped slots may be formed in respective central portions of the vertical plates. Each diagonal brace 22 may be oriented at angle of 45° or 60°, which allows convenience of construction and sufficient stress tolerance.

The foregoing description presents merely a few preferred embodiments of the present invention and is not intended to limit the scope thereof in any sense. Any and all changes and modifications made by those of ordinary skill in the art based on the above teachings also fall within the scope as defined in the appended claims.

What is claimed is:

1. A time-varying detecting method for concrete rheological parameters, comprising the steps of:

Step 1, providing a double-covered cylindrical container which has top and bottom covers that are allowed to be freely opened and closed, and a lifting frame including a pair of vertical supports each of which is rotatably connected by a connecting member to a side wall of the double-covered cylindrical container, wherein left bracket-shaped slots are formed in central portions of the vertical supports, and wherein each connecting member has an end received in a recess formed in an outer wall of the double-covered cylindrical container and tightly locked by an associated fastener, and a further end inserted in a respective one of the slots; wherein the left bracket-shaped slots each comprise a upper horizontal sub-slot, a lower horizontal sub-slot and a vertical sub-slot connecting an end of the upper horizontal sub-slot with an end of the lower horizontal sub-slot;

Step 2, opening the top cover of the double-covered cylindrical container to form an opening, and filling a prepared concrete mix into the double-covered cylindrical container through the opening;

Step 3, setting operating parameters for a concrete rheometer and activating the concrete rheometer to detect current static and dynamic rheological parameters of the concrete mix, and then deactivating the concrete rheometer;

Step 4, tightly closing the top cover of the double-covered cylindrical container and leaving the double-covered cylindrical container until a predetermined period of time expires;

Step 5, inserting and fixing opposing end portions of the connecting members respectively in the vertical supports and the recesses formed in the outer surface of the double-covered cylindrical container, lifting the double-covered cylindrical container to a predetermined height by raising the connecting members, flipping the double-covered cylindrical container 180°, and lowering the double-covered cylindrical container onto the floor;

Step 6, opening the bottom cover and re-mixing the concrete mix in the double-covered cylindrical container using a portable vane-type mixer until the concrete mix becomes homogeneous;

Step 7, repeating step 3 to detect time-varying rheological parameters of the concrete mix; and Step 8, deactivating the concrete rheometer and ending the process.

2. The method according to claim 1, wherein the rheological parameters comprises plastic viscosity and yield stress.

3. The method according to claim 1, wherein the predetermined period of time is one hour, two hours or three hours.

4. The method according to claim 1, wherein skirt bands are vertically spaced from one another across an inner wall of the double-covered cylindrical container.

5. The method according to claim 4, wherein the vertical supports includes parallel vertical plates and a foot plate to which the vertical plates are connected at bottoms, and wherein diagonal braces are provided where the vertical plates are connected to the foot plate.

* * * * *